US008885861B2

(12) United States Patent
Beck et al.

(10) Patent No.: US 8,885,861 B2
(45) Date of Patent: Nov. 11, 2014

(54) DEVICE FOR THE COMBINED APPLICATION OF A TRANSCUTANEOUS ELECTRICAL STIMULUS AND EMISSION OF AN ACOUSTIC SIGNAL

(71) Applicant: cerbomed GmbH, Erlangen (DE)

(72) Inventors: Christoph Beck, Moehrendorf (DE); Jens Ellrich, Langensendelbach (DE); Andreas Hartlep, Holzkirchen (DE); Wolf Gerhard Frenkel, Inzigkofen-Engelswies (DE)

(73) Assignee: Cerbomed GmbH, Erlangen (DE)

( * ) Notice: Subject to any disclaimer, the term of this patent is extended or adjusted under 35 U.S.C. 154(b) by 0 days.

(21) Appl. No.: 14/114,632

(22) Filed: Oct. 29, 2013

(65) Prior Publication Data

US 2014/0126752 A1 May 8, 2014

Related U.S. Application Data

(63) Continuation of application No. PCT/EP2012/001760, filed on Apr. 25, 2012.

(30) Foreign Application Priority Data

Apr. 30, 2011 (DE) .......................... 10 2011 100 065

(51) Int. Cl.
*H04R 25/00* (2006.01)
*H04R 1/10* (2006.01)
*A61N 1/36* (2006.01)
*A61F 11/00* (2006.01)

(52) U.S. Cl.
CPC .......... *H04R 1/1091* (2013.01); *A61N 1/36014* (2013.01); *A61N 1/36032* (2013.01); *H04R 25/75* (2013.01); *A61F 11/00* (2013.01); *A61N 1/361* (2013.01)
USPC .............. 381/326; 381/328; 381/151; 600/25

(58) Field of Classification Search
CPC .............. A61N 1/361; A61N 1/36017; A61N 1/36032; A61F 11/00; H04R 2225/021; H04R 25/75; H04R 25/606; H04R 2460/13; H04R 1/1091

USPC ......... 381/322, 326, 328, 330, 151, 380, 381; 600/25; 607/55, 56, 57
See application file for complete search history.

(56) References Cited

U.S. PATENT DOCUMENTS 6,198,971 B1 3/2001 Leysieffer
2005/0020873 A1 1/2005 Berrang et al.
(Continued)

FOREIGN PATENT DOCUMENTS

DE 10 2006 023 824 A1 11/2007
DE 10 2006 036 069 A1 1/2008

OTHER PUBLICATIONS

International Search Report of PCT/EP2012/001760 dated Aug. 31, 2012.

*Primary Examiner* — Huyen D Le
(74) *Attorney, Agent, or Firm* — Lucas & Mercanti, LLP

(57) ABSTRACT

The invention relates to a device for the combined application of a transcutaneous electrical stimulus to the surface of a portion of the human ear and emission of an acoustic signal into the auditory canal of the ear, wherein the device has at least one electrode head with at least one electrode for the application of the electrical stimulus, a loudspeaker and an output channel for acoustic signals into the auditory canal, a control device by which the application of the electrical stimulus and the emission of acoustic signals can be controlled. In order to achieve improved treatment of disorders using electrical stimulation, in particular tinnitus, the invention provides that the at least one electrode head which carries it is designed to allow it to be arranged in the Cymba conchae of the ear.

8 Claims, 3 Drawing Sheets

(56) References Cited

U.S. PATENT DOCUMENTS

Figure 1:
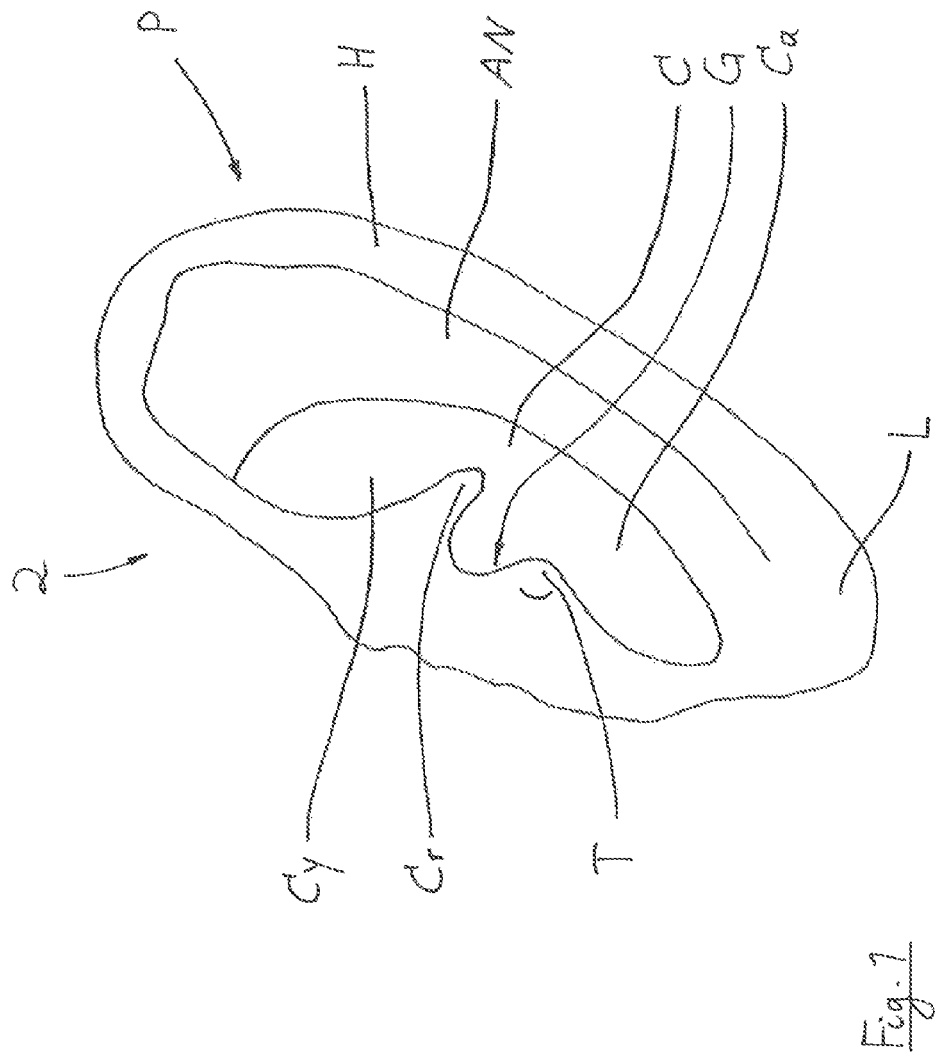

| | | |
|---|---|---|
| 2006/0015155 A1* | 1/2006 | Charvin et al. ................ 607/57 |
| 2006/0064139 A1 | 3/2006 | Chung et al. |
| 2006/0122675 A1 | 6/2006 | Libbus et al. |
| 2008/0021517 A1 | 1/2008 | Dietrich |
| 2008/0249594 A1 | 10/2008 | Dietrich et al. |
| 2011/0060383 A1* | 3/2011 | Lineaweaver et al. .......... 607/57 |
| 2013/0172662 A1* | 7/2013 | Menzl et al. .................... 600/25 |

* cited by examiner

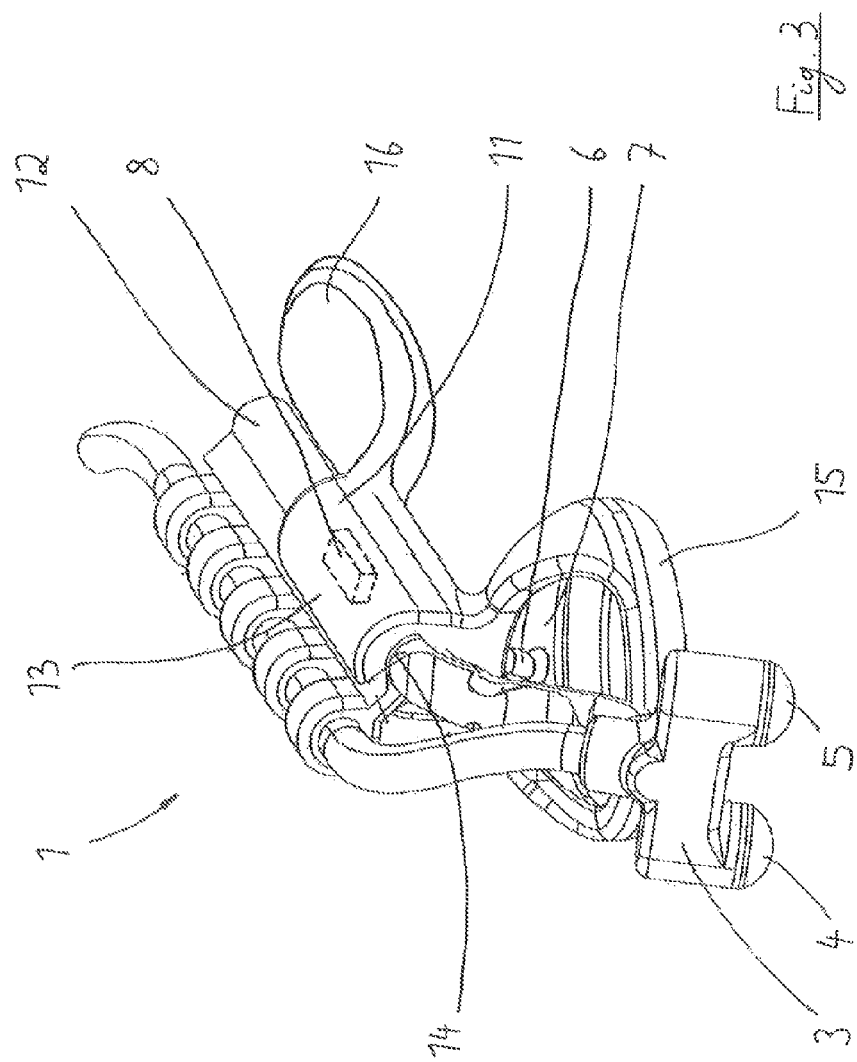

DEVICE FOR THE COMBINED APPLICATION OF A TRANSCUTANEOUS ELECTRICAL STIMULUS AND EMISSION OF AN ACOUSTIC SIGNAL

This application is a Continuation of PCT/EP2012/001760 filed Apr. 25, 2012, which claimed the priority of German Application No. 10 2011 100 065.1 filed Apr. 30, 2011. Both applications are incorporated herein by reference.

The invention relates to a device for the combined application of a transcutaneous electrical stimulus to the surface of a portion of the human ear and emission of an acoustic signal into the auditory canal of the ear, wherein the device comprises at least on electrode head with at least one electrode for the application of the electrical stimulus, wherein the device comprises a loudspeaker and an output channel for acoustic signals into the auditory canal and wherein the device further comprises a control device by which the application of the electrical stimulus and the emission of acoustic signals can be controlled.

A device of this kind is known from the DE 10 2006 036 069 B4. The device in form of an audiological transfer system, which is described there, provides a possibility of the transcutaneous nerve stimulation, particularly of the vagus nerve, wherein the application of an acoustical signal is also possible at the same time; in the mentioned case it is primary but not exclusively thought of the function of a hearing aid. For the transcutaneous nerve stimulation a bow-shaped extension is provided, which is inserted into the auditory canal of the ear. At the end of the extension an electrode head with two electrodes is provided.

Other solutions are described in US 2006/0064139 A1, in US 2008/0249594 A1, in US 2006/0122675 A1, in US 2005/0020873 A1 and in U.S. Pat. No. 6,198,971 B1.

It has shown that for certain applications the nerve stimulation which would be possible hereby, is not yet sufficient and disadvantageous respectively. It shall be indicated for example and especially the treatment of tinnitus, at which in general advantageous results can be achieved if the transcutaneous nerve stimulation is combined with the directed application of acoustical signals.

The transcutaneous nerve stimulation as such is described already in the DE 10 2006 023 824 B4. Here a device for the transcutaneous stimulation of the vagus nerves of the human body is disclosed, which device can be arranged in this case in the Pinna of the ear. The transcutaneous stimulation of the vagus nerve occurs here by contacting the tissue which has to be stimulated by using two spherical electrodes, which electrodes are elastically biased against the skin surface.

It is an object to the present invention, to provide a device of the kind which has been mentioned at the beginning, which device will allow it in an enhanced way, to enable an optimal treatment of diverse sicknesses, in particular of tinnitus, at which sicknesses a combined application of the transcutaneous nerve stimulation and emission of the acoustical signals is promising.

The solution of this object by the invention is characterized in that the at least one electrode or the electrode head which carries it is designed to allow it to be arranged in the Cymba conchae of the ear, that an elastic holding bow is arranged at the electrode head which is designed for encompassing the ear, and that the device further comprises a vibration generator by which mechanical vibrations can be applied onto a part of the osseous cranium, wherein the vibration generator is arranged on or integrated within the holding bow.

It has shown that the application of the transcutaneous electrical stimulus is particularly advantageous in the area of the Cymba conchae, if it will be combined with the application of the acoustical signals. The area of the Cymba conchae is thereby the area of the Concha of the ear, which area lies above of the Crus helicis; it is also named Hemiconcha superior. Below the Crus helicis downward the area of the Cavum conchae extends.

The electrode head with the at least one electrode is preferably designed kidney-shaped and comprises a substantial plane resting surface at the side facing the ear. Thereby it is provided especially preferred that the electrode head contacts the surface of the ear at a contact area which covers at least 50% of the surface of the Cymba conchae of the ear; a further preferred region covers even at least 80% of the surface of the Cymba conchae.

The output channel for acoustic signals is preferably designed as an extension at the electrode head.

With the vibration generator specifically mechanical vibrations can be applied onto the petrosal bone or onto the mastoid. Thereby, the two hearing test of Weber and Rinne (see below) can be carried out.

The control device can be designed to provoke chronologically agreed electrical stimulus via the electrodes and acoustical signals via the loudspeaker and if applicable mechanical vibrations via the vibration generator, wherein the chronological agreement comprises preferably simultaneous phases, time shifted phases and partially overlapping phases of electrical stimulus, signal and vibrations, if applicable. The control device comprises therefore preferably an electrical module for the provoking of electrical stimulus, acoustic signals and mechanical vibrations, if applicable.

The at least one electrode consists according to a further development at least partially of a synthetic material, which material is supplied with means for the establishment of electrical conductibility. Those means for the establishment of electrical conductibility can be electrical conductible particles, which particles are incorporated into the synthetic material; the means can also be at least one electrical conductible metal layer, which is applied galvanically on a base body of the electrode.

Furthermore, at least two electrodes can be provided, that is to say at least one stimulation electrode and one reference electrode, wherein the at least one stimulation electrode contacts the surface of the ear via a first contact surface and wherein the at least one reference electrode contacts the surface of the ear via a second contact surface, wherein the second contact surface is at least 3 times as large, preferably at least 5 times as large, as the first contact surface.

An alternative embodiment of the invention proposes a device for the combined application of a transcutaneous electrical stimulus to the surface of a portion of the human ear and emission of a mechanical vibration to a part of the osseous cranium, preferably to the petrosal bone or onto the mastoid, wherein the device comprises at least one electrode head with at least one electrode for the application of the electrical stimulus, wherein the device comprises a vibration generator for the production of mechanical vibrations, wherein the device further comprises a control device by which the application of the electrical stimulus and the emission of mechanical vibrations can be controlled and wherein the at least one electrode or the electrode head which carries them is designed to be able to be arranged in the Cymba conchae of the ear. Accordingly, the acoustic stimulation consists only of the vibration generator.

The mentioned electrode head though has preferably two electrodes, that is to say, a stimulation and a reference electrode (as depicted in the following embodiments). However, in general it can also be worked at the electrode head with only one single (stimulation) electrode; in this case a second (reference) electrode is arranged at another place, for example a neutral and indifferent respectively counter electrode in another area of the ear, but also in general at another part of the body, e.g. at the lower leg.

Thus, according to the invention it will be in particular pursued that the tonal tinnitus (in particular whistling, buzzing or chirr sounds) will be treated by the combination of transcutaneous stimulation of the vagus nerve and tones. This comprises also the treatment of tinnitus with other qualities, as pinging, swooshing, sounds of machines, buzzing, fizzling, clicking noise, knocking, either consistent or rhythmically pulsing, partially also pulse synchronically.

At the treatment of tinnitus the assignation of the height of the tone of the noise of the ear (comparative measurement with sinus sounds or narrow band noises) mostly takes place at first. Further an occlusion measurement can occur with sinus sounds or narrow band noises. Typically a noise which is conditioned to the inner ear can be covered here by sinus sounds or narrow band noises with a sound intensity level of 5 to 10 dB (until 20 dB) over the threshold. Further the measurement of the residual inhibition can occur. It is typical for noises which are conditioned to the inner ear, that the ear noise will be suppressed for several seconds after the completion of a covering with sinus sounds or narrow band noises and will appear only after that again.

When the frequency spectrum of an individual ear noise is objectively determined with adequate exactness, that noise can be copied artificially with a frequency generator (loud speaker) and the recessed frequencies together with a transcutaneous stimulation of the vagus nerve can be offered to the patient.

Possible ways of therapy are in this connection a periodical swelling and falling of the sound intensity of the offered sound or the mixture of the frequency, for example in form of the sinus.

Also possible is a sequential alternating, partially overlapping application of a sound therapy and the transcutaneous stimulation of the vagus nerve with the goal, to optimize a relearn effect of the brain.

Furthermore, a special sequence can occur with an application of the active identified sound frequencies over the concerned ear and also over the not (so strong) concerned ear for the exploitation of the so called crossover effects.

Furthermore, a vibrant application of the audio frequency can occur, either simultaneous to the likewise vibrated transcutaneous stimulation of the vagus nerve, alternating in the particular gaps of the likewise vibrated transcutaneous stimulation of the vagus nerve or simultaneous to the equal applied transcutaneous stimulation of the vagus nerve.

A vibrated application of the transcutaneous stimulation of the vagus nerve can occur either simultaneous to the likewise vibrated sound therapy, alternating in the particular gaps of the likewise vibrated sound therapy or simultaneous to the equal applied sound therapy.

At complex noises instead of the simultaneous application of the whole frequency band a frequency band can be provided which covers a sinus-like frequence passage from the highest to the deepest identified tinnitus frequency with a duration of several seconds.

Also, as a special application the addition of a transcranial magnet stimulation is possible as an intensifier for the retraining effect of the combined transcutaneous stimulation of the vagus nerve with the sounds.

Hereby, a description of a retraining program can occur which is applied over several days respectively weeks with a stimulation pattern which is tested respectively defined from day to day respectively from session to session individually for the patient, for example with exactly defined step-up and step-down sections.

Figure 2:
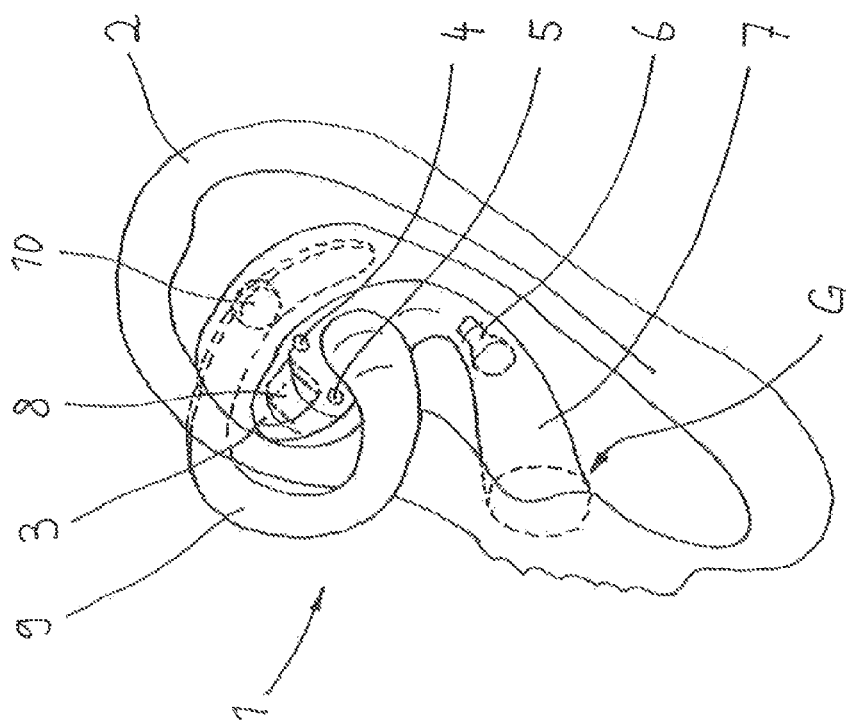

In the drawings embodiments of the invention are depicted. It shows:

FIG. 1 an ear conch (Pinna) of a human,

FIG. 2 the ear conch with a device for the application of an electrical stimulus and for the emission of an acoustic signal and FIG. 3 in a perspective view a device which is designed alternatively to FIG. 2 for the application of an electrical stimulus and for the emission of an acoustic signal.

In FIG. 1 an (outer) ear 2 of a human is depicted, which form is defined by the Pinna (ear conch) P. The Pinna P comprises in known manner the Helix H and the Antihelix AN; the Concha C is arranged centrally, which is limited sideways by the Tragus T. In the lower area the Lobule L is located. The Concha C is divided in an upper and a lower area; both areas are separated from each other by the Crus helicis Cr. The upper part of the Concha C is the Cymba conchae Cy, the lower part is the Cavum conchae Ca. The position of the ear canal is marked with G.

In the Pinna P a device 1 is arranged—as it is visible in FIG. 2—, by which device at the one hand a transcutaneous electrical stimulus can be executed on a part of the surface of the ear 2 and by which at the other hand an acoustical signal can be dispensed in the ear canal G.

With respect to the general design of a stimulation device of the vagus nerve, the described construction corresponds to the pre-known solution according to the above mentioned DE 10 2006 023 824 B4 of the applicant, on which explicitly reference is made insofar.

The device 1 is designed to be fixed at the area of the vagus nerve at the ear of the person who is using the device 1. Thereby a transcutaneous stimulation of the vagus nerve can be conducted.

Accordingly, the device 1 has an electrode head 3 with two electrodes 4 and 5, that is to say with a stimulation electrode 4 and a reference electrode 5. The electrode head 3 has a kidney-shaped design and is designed even at its side which is facing the ear, so that it can be placed in such a way in the ear, that it rests on the Cymba conchae Cy. As it can be seen in the synopsis of the FIGS. 1 and 2 this occurs in such a manner that the main area of the Cymba conchae Cy is covered by the electrode head 3.

The two electrodes 4, 5 are indicated as small punctual contacts in FIG. 2. It is also possible, that the electrode surface is much larger, wherein the electrodes can be defined in particular by two (or also several) areas, which expand laminar over the Cymba conchae.

That the device 1 will be held secure in the Pinna, a holding bow 9 is formed on the electrode head 3. The holding bow 9 at hand is designed as elastically, C-shaped part and reaches with its end behind the ear 2 in such a way, that it comes to lie upon the ear root and holds like this the device 1 in the Pinna.

Furthermore, at the electrode head 3 an output channel for acoustic signals 7 is arranged—which is designed as an extension of the electrode head—, which end is designed to be lead into the auditory canal G. In the output channel 7 a loudspeaker 6 is arranged at an adequate location.

The electrode head 3 forms a housing at the same time, in which housing at least a control device 8 is arranged, likewise preferably an electrical power supply (rechargeable battery). It is not depicted that in general it is also possible to conduct the control and the energy supply externally, wherefore then the device 1 comprises a cable to be supplied by an external control device and source of energy.

The device 1 comprises as a further element a vibration generator 10 for mechanical vibrations. This vibration generator is presently integrated into the holding bow 9. If the device 1 is arranged in the ear 2, the vibration generator 10 rests behind the ear at the area of the ear root. Accordingly, mechanical vibrations can be initiated directly into the osseous tissue of the brain cranium, so that a sound can be initiated into the inner ear which is placed in the petrosal bone, which can be noticed by the patient not by the auditory canal G but directly by the bone conduct.

The vibration generator 10 uses the same physiological principles like the so called Weber experiment. This experiment is an analysis for the conclusion of a lateralization of the auditory sensation by using a tuning fork. Together with the Rinne experiment it is a standard test in the ear, nose and throat medicine for the analysis of an auditory defect.

At the Weber experiment the foot of an oscillating tuning fork will be put on the crest of the patient. The sound will be transferred in-phase into both inner ears by the bone conduction. The person with normal hearing hears the sound of the tuning fork in both ears equally, he has therefore the impression to hear the sound in the middle of the head, the sound will not be lateralized. If the patient indicates to hear the sound only at one side, a lateralization exists, i.e. a unilateral or asymmetrical auditory defect is at hand.

At a unilateral sound sensation defect the sound will be discerned louder by the better hearing (normal) inner ear, thus the patient lateralizes into the healthy ear. At a unilateral sound conduction defect the sound will be indicated louder in the diseased ear because a retrograde acoustic emission only occurs by the healthy ossicle-chain.

Thus, with the Weber experiment a fast and reliable discernment is possible between sound sensation defect and sound conduction defect at a unilateral auditory defect, so for example between an acute hearing loss and a tympanic effusion. The sound initiation occurs particularly by the petrosal bone via bone conduction, not by the outer auditory canal (Meatus Acusticus Externus).

In FIG. 3 an alternative design of the device 1 can be seen but which design also underlies the principle to conduct the transcutaneous stimulation of the vagus nerve in the area of the Cymba conchae, while also an application with acoustical signals occurs next to the stimulation of the nerve. Accordingly, the above mentioned components of the device 1 are also given (not depicted is here the vibration generator 10, which though can just as well be provided here of course).

The device 1 has a holding element 11 as well as a holding rod 12 as essential components. The holding rod 12 carries the electrode head 3 at one axial end, which electrode head is provided with two electrodes 4, 5, that is to say with a stimulation electrode 4 and a (identically constructed) reference electrode 5. The holding element 11 has a central section which section is dominated by a linear guide 13. Here it is about a material section with a form like a bar, which extends itself in a longitudinal direction, in which a circular recess 14 is formed in.

At the front end of the linear guide 13 a resting part 15 is formed on; at the rear end, a cheek rest 16 is at hand. The resting part 15 comprises a circular section; the cheek rest 16 is designed at hand as an even section and serves as an additional stabilization for the resting of the device 1. The holding element 11 is able to shift the holding rod 12 into the direction of the longitudinal axis by means of the linear guide 13.

The loud speaker 6 here lies above the circular resting part 15, so that an output channel 7 will be formed here in form of a sound element, by which sounds of the loud speaker 6 can attain into the auditory canal. The ring-shaped resting part 15 lies exactly over the auditory canal opening when the device 1 is applied. The loud speaker 6 can fill out the whole ring of the resting part 15.

In both embodiments according to FIG. 2 and FIG. 3 electrodes with the same size 4, 5 are provided, which electrodes can be formed hemispherically. But also a variation of this is possible. The stimulation and reference electrodes can respectively have a form which is adapted to the area respectively to the surface of the ear 2, where they shall be placed at. Oval or kidney-shaped structures can be previewed here. The at least two electrodes contact the surface of the ear 2 and namely the Cymba conchae with respective contact surfaces. In doing so, one of the contact surfaces can be considerably larger than the other one. Experiments have showed that advantageous effects can be reached if one of the areas is at least 3 times as large as the other area. The electrodes 4, 5 are thereby arranged at a distance. The minimal distance is mostly 5 mm. But also distances up to 50 mm can be previewed.

The invention can be defined by one or more of the following items wherein the reference characters are used for clarity.

1. Device (1) for the combined application of a transcutaneous electrical stimulus to the surface of a portion of the human ear (2) and emission of an acoustic signal into the auditory canal (G) of the ear (2), wherein the device (1) comprises at least on electrode head (3) with at least one electrode (4, 5) for the application of the electrical stimulus, wherein the device (1) comprises a loudspeaker (6) and an output channel (7) for acoustic signals into the auditory canal (G) and wherein the device further comprises a control device (8) by which the application of the electrical stimulus and the emission of acoustic signals can be controlled, characterized in that the at least one electrode (4, 5) or the electrode head (3) which carries it is designed to allow it to be arranged in the Cymba conchae (Cy) of the ear (2).

2. Device according to item 1, characterized in that the electrode head (3) with the at least one electrode (4, 5) is designed kidney-shaped and comprises a substantial plane resting surface at the side facing the ear, wherein the electrode head (3) preferably contacts the surface of the ear (2) at a contact area which covers at least 50% of the surface of the Cymba conchae (Cy) of the ear (2).

3. Device according to items 1 or 2, characterized in that the output channel (7) for acoustic signals is designed as an extension at the electrode head (3).

4. Device according to one of items 1 to 3, characterized in that an elastic holding bow (9) is arranged at the electrode head (3) which is designed for encompassing the ear (2).

5. Device according to one of items 1 to 4, characterized in that it further comprises a vibration generator (10) by which mechanical vibrations can be applied onto a part of the osseous cranium, preferably onto the petrosal bone or onto the mastoid.

6. Device according to items 4 and 5, characterized in that the vibration generator (10) is arranged on or integrated within the holding bow (9).

7. Device according to one of items 1 to 6, characterized in that the control device (8) is designed to provoke chronologically agreed electrical stimulus via the electrodes (4, 5) and acoustical signals via the loudspeaker (6) and if applicable mechanical vibrations via the vibration generator (10), wherein the chronological agreement comprises preferably simultaneous phases, time shifted phases and partially overlapping phases of electrical stimulus, signal and vibrations, if applicable.

8. Device according to item 7, characterized in that the control device (8) comprises an electrical module for the provoking of electrical stimulus, acoustic signals and mechanical vibrations, if applicable.

9. Device according to one of items 1 to 8, characterized in that the at least one electrode (4, 5) consists at least partially of a synthetic material, which material is supplied with means for the establishment of electrical conductibility, wherein the means for the establishment of electrical conductibility are preferably electrical conductible particles, which particles are incorporated into the synthetic material or wherein the means for the establishment of electrical conductibility are at least one electrical conductible metal layer, which is applied galvanically on a base body of the electrode (4, 5).

10. Device according to one of items 1 to 9, characterized in that at least two electrodes (4, 5) are provided, that is to say at least one stimulation electrode (4) and one reference electrode (5), wherein the at least one stimulation electrode (4) contacts the surface of the ear (2) via a first contact surface and wherein the at least one reference electrode (5) contacts the surface of the ear (2) via a second contact surface, wherein the second contact surface is at least 3 times as large, preferably at least 5 times as large, as the first contact surface.

11. Device (1) for the combined application of a transcutaneous electrical stimulus to the surface of a portion of the human ear (2) and emission of a mechanical vibration to a part of the osseous cranium, wherein the device (1) comprises at least one electrode head (3) with at least one electrode (4, 5) for the application of the electrical stimulus, wherein the device (1) comprises a vibration generator (10) for the production of mechanical vibrations, wherein the device (1) further comprises a control device (8) by which the application of the electrical stimulus and the emission of mechanical vibrations can be controlled and wherein the at least one electrode (4, 5) or the electrode head (3) which carries them, is designed to be able to be arranged in the Cymba conchae (Cy) of the ear (2).

LIST OF REFERENCES

1 Device
2 Ear
3 Electrode head
4 Electrode
5 Electrode
6 Loudspeaker
7 Output channel for acoustic signals (sound element)
8 Control device
9 Holding bow
10 Vibration generator
11 Holding element
12 Holding rod
13 Linear guide
14 Circular recess
15 Resting part
16 Cheek rest
G Auditory canal
Cy Cymba conchae
AN Antihelix
C Concha
Ca Cavum conchae
Cr Crus helicis
H Helix
L Lobule
P Pinna
T Tragus

The invention claimed is:

1. A device for the combined application of a transcutaneous electrical stimulus to the surface of a portion of the human ear and emission of an acoustic signal into the auditory canal of the ear, wherein the device comprises:
   at least on electrode head with at least one electrode for the application of the electrical stimulus;
   a loudspeaker and an output channel for acoustic signals into the auditory canal;
   a control device by which the application of the electrical stimulus and the emission of acoustic signals can be controlled;
   the at least one electrode or the electrode head which carries it is designed to allow it to be arranged in the Cymba conchae of the ear;
   an elastic holding bow is arranged at the electrode head which is designed for encompassing the ear; and
   a vibration generator by which mechanical vibrations can be applied onto a part of the osseous cranium, wherein the vibration generator is arranged on or integrated within the holding bow.

2. The device according to claim 1,
wherein the electrode head with the at least one electrode is designed kidney-shaped and comprises a substantial plane resting surface at the side facing the ear, wherein the electrode head contacts the surface of the ear at a contact area which covers at least 50% of the surface of the Cymba conchae of the ear.

3. The device according to claim 1,
wherein the output channel for acoustic signals is designed as an extension at the electrode head.

4. The device according to claim 1,
wherein by means of the vibration generator mechanical vibrations can be applied onto the petrosal bone or onto the mastoid.

5. The device according to claim 1,
wherein the control device is designed to provoke chronologically agreed electrical stimulus via the electrodes and acoustical signals via the loudspeaker and if applicable mechanical vibrations via the vibration generator, wherein the chronological agreement comprises simultaneous phases, time shifted phases and partially overlapping phases of electrical stimulus, signal and vibrations.

6. The device according to claim 5,
wherein the control device comprises electronic module for the provoking of electrical stimulus, acoustic signals and mechanical vibrations.

7. The device according to claim 1,
wherein the at least one electrode consists at least partially of a synthetic material, which material is supplied with means for the establishment of electrical conductibility, wherein the means for the establishment of electrical conductibility are electrical conductible particles, which particles are incorporated into the synthetic material or wherein the means for the establishment of electrical conductibility are at least one electrical conductible metal layer, which is applied galvanically on a base body of the electrode.

8. The device according to claim 1,
wherein at least two electrodes are provided, that is to say at least one stimulation electrode and one reference electrode, wherein the at least one stimulation electrode contacts the surface of the ear via a first contact surface and wherein the at least one reference electrode contacts the surface of the ear via a second contact surface, wherein the second contact surface is at least 3 times as large as the first contact surface.

* * * * *